United States Patent [19]

Fischer et al.

[11] Patent Number: 4,851,578
[45] Date of Patent: Jul. 25, 1989

[54] PREPARATION OF TRIALKYLAMINES

[75] Inventors: Roman Fischer, Mutterstadt; Herbert Mueller, Frankenthal, both of Fed. Rep. of Germany

[73] Assignee: BASF Aktiengesellschaft, Ludwigshafen, Fed. Rep. of Germany

[21] Appl. No.: 78,288

[22] Filed: Jul. 27, 1987

[30] Foreign Application Priority Data

Aug. 14, 1986 [DE] Fed. Rep. of Germany ....... 3627592

[51] Int. Cl.$^4$ ............................................. C07C 85/06
[52] U.S. Cl. .................................. 564/479; 564/480
[58] Field of Search ................................ 564/479, 480

[56] References Cited

U.S. PATENT DOCUMENTS

| | | | |
|---|---|---|---|
| 2,953,601 | 9/1960 | Whitaker et al. | 564/479 |
| 3,223,734 | 12/1965 | Fallstad et al. | 564/480 |
| 3,366,687 | 1/1968 | Ellis et al. | 564/479 |
| 3,708,539 | 1/1973 | Fenton et al. | 564/479 |
| 3,720,715 | 3/1973 | Nicholl | 564/479 |
| 3,803,239 | 4/1974 | Feichtinger et al. | 564/479 |
| 3,804,901 | 4/1974 | Noeske et al. | 564/480 |
| 4,009,124 | 2/1977 | Laurer et al. | 564/479 |
| 4,234,727 | 11/1980 | Toussaint et al. | 564/479 |
| 4,480,131 | 10/1984 | Klier et al. | 564/480 |

FOREIGN PATENT DOCUMENTS

| | | | |
|---|---|---|---|
| 1212963 | 10/1986 | Canada | 564/479 |
| 0009590 | 4/1980 | European Pat. Off. | 564/479 |
| B13176 | 7/1980 | European Pat. Off. | 564/479 |
| B24225 | 7/1981 | European Pat. Off. | 564/479 |
| B70512 | 6/1984 | European Pat. Off. | 564/479 |
| 0227904 | 7/1987 | European Pat. Off. | 564/479 |
| 2114614 | 4/1974 | Fed. Rep. of Germany | 564/479 |
| 2625196 | 12/1977 | Fed. Rep. of Germany | 564/479 |
| 2709864 | 8/1978 | Fed. Rep. of Germany | 564/479 |
| 3246978 | 6/1984 | Fed. Rep. of Germany | 564/479 |

OTHER PUBLICATIONS

Russian Chemical Reviews, 34 (1965), pp. 843–853.
Catalysis Reviews Science & Engineering, 27(4), 1985, pp. 653–697.
Ind. Eng. Chem. Prod. Dev., 22(1983), No. 2, pp. 217–225.

*Primary Examiner*—Werren B. Lone
*Attorney, Agent, or Firm*—John H. Shurtleff

[57] ABSTRACT

Trialkylamines are prepared by reacting primary alcohols with ammonia or a primary alkylamine in the presence of a hydrogenation/dehydrogenation catalyst and in the presence of hydrogen by (a) operating in liquid phase
(b) using the alcohol in a stoichiometric excess of from 1 to 15 moles per mole of ammonia or primary alkylamine,
(c) carrying out the reaction in the presence of the water formed in the course of the reaction, and
(d) using a hydrogenation/dehydrogenation catalyst which substantially contains only copper as the catalytically hydrogenating/dehydrogenating metal.

10 Claims, No Drawings

PREPARATION OF TRIALKYLAMINES

The present invention relates to a process for preparing a trialkylamine by reacting a primary alcohol with ammonia in the presence of a hydrogenation/dehydrogenation catalyst.

The catalytic alkylation of amines with alcohols has been known for a long time. The catalysts used and recommended for this reaction are on the one hand dehydrating oxides, for example of aluminum, thorium, tungsten or chromium, and on the other hydrogenation/dehydrogenation catalysts based, for example, on copper, nickel, cobalt or chromium. Liquid-phase and gas-phase processes are known. A detailed description of the field is given in a paper by V.A. Nekrasova and N.I. Shuikin in Russian Chemicals Reviews 34 (1965), 843 and in The Acyclic Aliphatic Tertiary Amines, L. Spialter and J.A. Pappalardo, Macmillan, 1965. A recent paper by A. Baiker and Jacek Kijenski in Catal. Rev.-Sci. Eng. 27 (1985), 653-697 gives a further detailed account.

Tertiary amines are prepared by alkylation of ammonia, primary amines or secondary amines with alcohols. As a consequence of transalkylation/disproportionation reactions, the reacted mixtures contain not only the desired tertiary amines but also secondary and primary amines as byproducts, frequently in high concentrations. It is particularly difficult to prepare the tertiary amines from ammonia and alcohols. Commercially available tertiary amines such as triethylamine, tripropylamine, tributylamine or trioctylamine are industrially always prepared from ammonia and a corresponding alcohol. The tertiary amines are always obtained together with primary and secondary amines. In this reaction, it is necessary for the ammonia to be present in excess compared with the alcohol component, so that the aldol condensation of the carbonyl compounds formed as intermediates from the alcohols can be kept within limits. On the other hand, the excess ammonia naturally inhibits the formation of the tertiary amine, which is also true if amines are used in place of ammonia.

If a relatively high demand for tertiary amines is to be covered, a frequently applied remedy is to subject primary or, better, secondary amines in a separate stage to a further alkylation with alcohols. Such a process is described in DE-A-1,493,781, at least stoichiometric amounts of the secondary amine being reacted with the alcohol. The amine to be converted is thus intended to be present in the reaction zone in an at least equimolar amount compared with the alcohol. It is demonstrated that an excess of alcohol results in poor selectivitiy in respect of the tertiary amine formed. This prior art is another confirmation of the principle which is always employed in industry, namely to obtain high selectivities by using the nitrogen component in excess. It is true that the reaction of secondary alcohols using such a measure appears to improve the selectivity for the amine to a certain extent, but the conversion of the amine is low. Primary alcohols always lead to low conversions and a poor selectivity, since the byproducts formed are in this case residues which reduce the yield.

An improved process for preparing tertiary amines is described in U.S. Pat. No. 3,708,539; an alcohol is reacted in liquid phase with a secondary amine over catalysts based on ruthenium, osmium, rhenium or technetium. The disadvantage of this process is the fact that conversion and yield, based on the starting alcohols and measured against the cost of the catalyst raw materials, are inadequate for an industrial process.

Tertiary amines of the type of the dimethyl fatty alklyamines whose fatty alkyl radical in general has more than 8 carbon atoms, in particular, are industrially interesting. These products are produced in a large volume by a very wide range of methods, partly in the gas phase and partly in the liquid phase.

The synthesis of low molecular weight tertiary alkylamines is more difficult.

Typical representatives of this class of compounds are for example dimethylethylamine and triethylamine. These tertiary amines are used industrially in large volumes as catalysts for speeding up the polymerization of polyurethane resins, for example in foundry core binders. Further tertiary amines of this class of product are for example n-propyldimethylamine, methylethyl-n-propylamine, isopropyldimethylamine or n-butyldimethylamine. Hitherto all attempts to prepare these low molecular weight tertiary amines by the method which is successful in the synthesis of long-chain amines have been failures. For that reason it was proposed in DE-A-2,838,184 and EP-B-24,225 that the synthesis of these compounds be carried out by reaction in the gas phase, for example from dimethylamine and the corresponding low molecular weight alcohols, either over copper/chromite catalysts or over pure copper catalysts formed by thermal decomposition or reduction of basic copper aluminum carbonates. Health reasons, however, argue against the use of chromite catalysts, since they are carcinogenic. Gas phase processes have in general the disadvantage that, to carry out the gas phase reaction, a comparatively high energy input is required for evaporating the reactants and maintaining a sufficiently large gas stream to prevent condensation on the catalyst. In addition, separating the target product from the recirculating gas requires a sizable engineering input in condensation, usually in the form of successive multistage condensations. Since these processes are carried out in the gas phase under relatively low hydrogen partial pressures over catalysts having not only a hydrogenating action but also a dehydrogenating action, the alcohol is to some extent also converted into the corresponding aldehyde which, by aldol condensation, leads to the unwanted alkyl group with twice the number of carbon atoms and hence to byproducts which not only reduce the yield but also appear as impurities in the end product. The formation of acetaldehyde from ethanol and the formation of $C_4$ radicals is for example described in those terms in EP-B-24,225.

U.S. Pat. No. 4,480,131 likewise describes a gas phase process for preparing secondary and also, to a minor extent, tertiary amines by alkylation of primary amines with alcohols. Working with excess amine is preferred. Nevertheless, the reaction is not very selective. In addition, the conversions are incomplete and, as all the examples given therein show, disproportionation reactions leading to the formation of ammonia are found to be prominent.

There have also been repeated attempts to convert ammonia directly into a tertiary amine by alkylation with an alcohol in the presence of a hydrogenation/dehydrogenation catalyst. U.S. Pat. No. 2,953,601 descibes the reaction under atmospheric pressure, the water of reaction being continuously removed as an azeotropic mixture with the excess alcohol, and recovered alcohol being returned into the reaction vessel. If the water of reaction is not removed, the reaction ceases. The method described produces a tertiary amine yielded of from 58 to 65%. However, the proportion of primary and secondary amines and byproducts is appreciable.

A two-stage process as described in U.S. Pat. No. 3,223,734 is intended to avoid these disadvantages. In a first step, a saturated alcohol of 4 to 22 carbon atoms is reacted with ammonia in the presence of a hydrogenation/dehydrogenation catalyst, and thereafter the resulting mixture of primary, secondary and tertiary amines and of unconverted alcohol has added to it further alcohol, so that sufficient alcohol is present for stoichiometric conversion to tertiary amines. In a second reaction step, the mixture is then treated within the temperature range from 190° to 230° C. in the same way as in the first stage to convert the primary and secondary amines obtained in the first stage into tertiary amines by azeotropic removal of the water of the reaction. It is true that tertiary amine yields of up to 98% are reported, but analysis by means of gas chromatography shows that the amines are very highly contaminated. Distillation does not isolate them in sufficiently pure form. The amines are found to contain alkyl groups having twice the number of carbon atoms compared with the starting alcohols. In addition, there are some other byproducts such as carboxamides, secondary amines and other substances. Even careful distillation of the crude amine mixture obtained does not result in the sort of purity required for example of products to be used in hydrometallurgy. The selectivity of the amines for metal ions is considerably impaired by the presence of substances such as carboxamides, nitriles, hydrocarbons and acetals.

DE-A-2,057,001 describes a process for preparing tertiary amines from ammonia and primary alcohols in the presence of hydrogenation/dehydrogenation catalysts. In this process it is necessary to continuously remove the water formed in the course of the reaction. The recycle gas method is employed, which is disadvantageous because of the increased thermal and mechanical energy input required. It is true that the process of DE-A-2,057,001 produces high selectivities in the reaction of alcohols with ammonia, but the activity of the catalysts pretreated with a primary, secondary or tertiary amine is not sufficient to be able to dispense with the continuous removal of the water of reaction during the reaction. The recommended catalysts are those based on nickel, cobalt or iron. Of particular interest is the experimental result in part 2 of Example 2 of this DE-A specification, according to which, if ammonia is absent, about half the isononanol alcohol used is converted by the catalyst into isononanal diisononanol acetal. This observation, in particular if seen together with the prior art discussed above, argues that ammonia should always be used in excess to prevent such undesirable reactions.

It is an object of the present invention to provide a process of the type mentioned at the beginning, which does not have the disadvantages of the prior art, which permits the preparation of a very pure tertiary amine in a high yield and which makes it possible to obtain the necessary purity in a very simple distillation.

We have found that this object is achieved with a process for preparing a trialkylamine by reacting a primary alcohol with ammonia or a primary alkylamine in the presence of a hydrogenation/dehydrogenation catalyst and in the presence of hydrogen, which comprises (a) operating in liquid phase,
(b) using the alcohol in a stoichiometric excess of from 1 to 15 moles per mole of ammonia of primary alkylamine,
(c) carrying out the reaction in the presence of the water formed in the course of the reaction, and
(d) using a hydrogenation/dehydrogenation catalyst which substantially contains only copper as the catalytically hydrogenating/dehydrogenating metal.

The process according to the invention can be carried out in simple, uncomplicated and therefore inexpensive reaction apparatus in a virtually quantitative yield. The energy input required is small. The crude reaction mixture can be worked up in a simple manner to the desired pure target product. The copper catalyst to be used is inexpensive and has a very long life. In the process according to the invention, the formation of undesirable byproducts is suppressed, the useful product being obtained in high selectivity.

Although the water formed in the course of the reaction substantially remains in the reaction mixture, this reduces neither the yield of product nor the rate of reaction; on the contrary, yield and rate of reaction unexpectedly increase.

It was not foreseeable for the process according to the invention, but is of pivotal significance, that, unlike the process of DE-A-2,075,001, if the reaction parameters according to the invention are complied with the dehydrogenating effect of the catalyst on the alcohol is nonexistent even in the absence of ammonia. While under the comparable process conditions of DE-A-2,075,001 about half the alcohol is consumed in secondary reactions, such a loss does not take place under the reaction conditions according to the invention.

The high selectivity for the formation of the tertiary amine in the process according to the invention is at variance with the result reported by A. Baiker and J. Kijenski in the above-cited reference. According to them, ammonia and octanol over copper catalysts at 240° C. give after reaction a mixture containing 21% by weight of octanol, 25% by eight of octylamine, 30% by weight of dioctylamine, 7% by weight of trioctylamine, 14% by weight of caprylonitrile and 3% by weight of byproducts. A similar product distribution is also obtained in the cases of dodecanol and decanol (see page 690 of said publication).

Compared with the result of aminating ethanol with ammonia to ethylamines as reported in EP-B-13,176, the process according to the invention has a surprisingly high selectivity in respect of the tertiary amine which is obtained if the prescribed reaction parameters according to the invention are complied with. In EP-B-13,176, alcohol and ammonia are essentially converted to the primary amine.

The process according to the invention makes use of a catalyst which, as active component, substantially contains only copper, either as a fixed bed or in suspended form. The reactants are advantageously brought together in the presence of an alkali metal oxide and/or hydroxide and/or alkaline earth metal oxide and/or hydroxide dissolved or suspended in liquid phase. Said alkali or alkaline earth metal oxide or hydroxide can be the oxide or or hydroxide or lithium, sodium, potassium, magnesium, calcium, srontium, barium or a mixture thereof.

The total pressure has to be sufficiently high for the reactants to form a substantially liquid phase. Depending on the nature of the starting materials, the total pressure ranges from about 50 to 300 bar, preferably from 50 to 200 bar, of which from about 10 to 50% are accounted for by the hydrogen partial pressure.

Unlike existing processes, it is not necessary according to the invention to continuously remove the water formed in the course of the reaction to obtain complete conversion of ammonia. This last result in particular was not foreseeable for the reaction in liquid phase since it is known from many other cases (cf. for example DE-C-2,625,196) that complete alkylation is only possible if water is removed from the reaction mixture as it is formed.

Using the process according to the invention, it is possible to react in particular monohydric aliphatic alcohols having 2 to 24 carbon atoms, such as ethanol, n-propanol, i-propanol, n-butanol, n-heptanol, n-dodecanol or, for example, stearyl alcohol, in the presence or absence of hydrogen, with ammonia to the corresponding tertiary trialkylamine in an almost quantitative yield. Instead of a pure alcohol, it is also possible to use alcohol mixtures.

Lastly, it is also possible to start the reaction with a certain alcohol and, before the alkylation of the ammonia is complete, to add to the reaction mixture a further alcohol which is different from the first alcohol. As a result, a certain alkyl distribution is obtained on the tertiary amine. Although it is known that copper catalysts very highly favor the disproportionation of the alkylamine, it is possible by maintaining the parameters according to the invention, in particular by adding the abovementioned alkaline substance in the liquid phase, to substantially avoid this disproportionation reaction. The addition of such an alkaline substance to the fixed bed catalyst as described for example in EP-B-13,176 does not prevent the disportionating action of the copper catalyst. The copper catalyzed disproportionation of alkylamines is dealt with in Ind. Eng. Chem. Prod. Res. Dev., 22, 2 (1983), 219. In the practice of the process according to the invention, primary amines are found at most in traces and secondary amines only in minor amounts.

The process can be carried out over a fixed bed catalyst, whether as a liquid phase process or as a trickle phase process, or over a suspended catalyst.

The fixed bed catalyst process is advantgeously carried out as follows:

The reactor used is for example an upright cylindrical vessel equipped with the customary cooling or heating means and with a facility for feeding in the reactants. The reaction vessel is packed with the catalyst, which can be of any desired shape. Frequently, the catalyst used is in the form of extrudate of from 3 to 6 mm in diameter and of up to 6 cm in length. However, the catalyst can also be used in tablet form in the shape of cylinders or for example 5 mm in diameter and 5 mm in height or as a sphere or in any other desired shape.

In the trickle phase method, the reactants ammonia and alcohol trickle downward through the catalyst-containing reaction vessel, for example at a rate of from 200 to 500 ml of reaction mixture per liter of catalyst volume per hour. The reaction pressure is brought to the desired value resulting from the vapor pressure of the reactants and reaction products, the hydrogen partial pressure and any additionally employed inert gas pressure.

The discharge of offgases is substantially unnecessary, since the process according to the invention, virtually does not lead to the formation of foreign inert gases. In this respect the process is particularly economical in hydrogen consumption. The decarbonylation of the carbonyl intermediate formed from the alcohol, which occurs with most amination processes, virtually does not take place in the process according to the invention.

The product leaving the reaction zone passes into a level-controlled receiver, from where the product mixture is removed, preferably batchwise. Since the reaction is slightly exothermic at about 14 kcal/mol, the reaction vessel can be maintained under isotheremal conditions by returning a portion of the reaction product by means of a centrifugal pump to the catalyst bed after prior cooling. The reaction is advantageously carried out in such a way that all the starting ammonia is converted. In this way it is possible to save on investment and avoid operating a costly ammonia return column. Instead, the pure trialkylamine is isolated by simple distillative separation from the alcohol used in excess, which is returned into the reaction. Since the reaction is not harmed if small amounts of water of reaction are returned into the reaction together with the alcohol, the distillative workup in the process according to the invention is extremely simple.

Although industrially of minor importance, in one version of the process according to the invention the ammonia can also be replaced by a primary, in particular low molecular weight, amine having 1 to 6 carbon atoms for the preparation of a tertiary trialkylamine. This reaction is of importance in particular for synthesis of mix-alkylated tertiary amines. This version of the process is advantageous compared with all the other disclosed processes, since no alkyl disproportionation whatever is observed, provided the temperature range employed is not too extreme (reaction temperature below 240° C.). However, the reaction of ammonia with the alcohols is deemed to be technically and economically more important.

In addition to the preferred use of the trickle phase method described above, the reaction can also be carried out in such a way that the reactants flow upward in liquid from through the catalyst bed (liquid phase method). In this case too the heat of reaction may be dissipated by recycling. As with the trickle phase method, it is also possible to arrange for isothermal reaction control by way of the reactant used in excess.

A preferred embodiment of the process according to the invention is carried out with copper catalysts as described in DE-A-2,445,303. They can be regarded as amorphous products of the thermal decomposition and reduction of basic copper/aluminum compounds and can be obtained by adding an alkali metal carbonate at pH 8 to 10 to a dilute solution of a copper and aluminum salt whose molarity is advantageously below 3, and decomposing the precipitates obtained, before or after appropriate molding, at from 350° to 600° C. Customary reduction, preferably in the presence of the alcohol used in the subsequent reaction, gives highly active catalysts which are most suitable for the present process. However, it is also possible to use copper catalysts obtained by impregnating a suitable support material, for example pumice, diatomaceous earth, silica gel, thorium oxide or aluminum oxide, and subsequent reduction.

The process according to the invention can also be carried out as a suspension process, where the reduced copper catalyst is suspended in the reactants alcohol, ammonia or monoalkylamine. Suitable catalysts are for example Raney copper or the copper catalysts described above in pulverulent form. However, preference is given to active copper material obtained by heating copper formate at from 200° to 250° C. in the presence of an alcohol and of a dialkylamine. The preparation of such a catalyst is described for example in EP-B-70,512.

The tertiary amine is synthesized according to the invention in the presence of a stoichiometric excess of an alcohol over ammonia or an amine of, by definition, not less than about 1 mole. In the case of ammonia, the molar ratio alcohol:ammonia thus ranges from 4:1 to 18:1, and in the case of the primary amines this ratio ranges from 3:1 to 17:1, although the upper limits are not critical, being merely dictated by economics. The excess level can easily be optimized in a few experiments, the general rule being that the excess increases with increase in molecular weight of the alcohol.

A very advantageous measure with the present process is to add alkaline earth and/or alkali metal oxide or hydroxide to the liquid reactants.

With this measure it is possible to achieve virtually complete suppression or transalkylation reactions and disproportionations. In general, the highest effectiveness is obtained when the bases are dissolved in the reaction mixture, although a suspension will also be satisfactory. A distinctly smaller effect is observable on using copper catalysts which are doped with the bases; consequently, the bases should ideally be present in the free form.

The reaction is advantageously carried out at from 190° to 280° C. The preferred range extends from 200° to 240° C.

The rate of reaction is very high: without difficulty it is possible to produce from 100 to 600 parts by weight of tertiary trialkylamine per liter of catalyst volume per hour.

In the practice of the process according to the invention it was found, surprisingly for an amination, that the activity of catalysts is preserved unchanged for extremely long periods. In fixed bed catalysis, for example, the preferred copper catalyst, described in DE-A-2,445,303, can be kept onstream for more than a year.

EXAMPLE 1

For the continuous preparation of triethylamine, a feed mixture was prepared from 7,309 of ethanol azeotrope (95.6% by weight of ethanol, 4.4% by weight of water and 1.2% by weight of toluene as a denaturant) and 289 g of ammonia together with 0.025% by weight of 50% strength sodium hydroxide solution.

The amination was carried out in an upright reaction tube of 1,000 ml capacity. The ratio of the diameter to the length of the tube was 1:40. The tube was thermostatable by means of an organic heat transfer medium pumped into a heating jacket. The reaction tube was packed with 700 ml of a catalyst bed. The catalyst particles had the shape of cylinders which were 3 mm in length and 3 mm in diameter. The catalyst had been prepared in accordance with the directions of Example 1 of DE-A-2,445,303. The catalyst was reduced at from 180° to 200° C. with hydrogen while at the same time 300 ml of ethanol per hour were trickled over the catalyst. The reduction of the catalyst was initially carried out with a hydrogen/nitrogen mixture (50 bar) and later with pure hydrogen until no more water of reduction was detectable in the ethanol azeotrope runoff. The oven was then charged at 250° C. at the top with 300 g of the above-described ammonia-containing feed per hour under total pressure of 200 bar (hydrogen partial pressure <150 bar). At the top of the receiver 900 ml (atmospheric pressure) of hydrogen were removed per hour as offgas. The reaction product leaving the receiver was analyzed by gas chromatography and distillation and found to have the following composition (calculated on a water-free basis):

Diethylamine: <0.5% by weight
Triethylamine: 23% by weight
Ethanol: 76% by weight
Unknowns and
residues: <0.5% by weight By distillation this crude mixture can be made to yield triethylamine of over 99.9% purity.

A similar result was obtained with the same molar amounts of potassium hydroxide and lithium hydroxide in place of sodium hydroxide.

Using a copper-impregnated catalyst (20% by weight of Cu on silica gel) and a reactants feed of around 150 g/h likewise produced virtually the same result.

EXAMPLE 2

To synthesize tri-n-pentylamine, a solution of 1 mol of n-pentylamine in 4 mol of n-pentanol was prepared. This solution was treated with 0.25% by weight of 50% strength by weight sodium hydroxide solution.

The amination was carried out in the apparatus described in Example 1. The reaction temperature ranged from 230° to 235° C., and the total pressure was 60 bar, of which around 10 bar were accounted for by the hydrogen partial pressure. The feed rate of reactants was maintained at 300 ml per hour and the offgas rate at 500 ml per hour.

The reaction product obtained was subjected to a distillation analysis and found to have the following composition (water of reaction not included):

n-Pentanol: 51% by weight
Tri-n-pentylamine: 45% by weight
Di-n-pentylamine 3% by weight
Total unknowns: 0.8% by weight
High boilers: 0.2% by weight By fractional distillation it was possible to isolate the tripentylamine in over 99.5% purity.

EXAMPLE 3

First a solution was prepared at room temperature from 8 mol of n-butanol and 1 mol of ammonia. This solution was treated with 0.05% by weight of 50% strength by weight sodium hydroxide solution.

The amination was carried out in the apparatus described in Example 1 at 230° C. with a feed rate of 300 g per hour. The total pressure in the course of the synthesis was 200 bar and the hydrogen partial pressure . . . bar, the hourly offgas rate being 500 ml under atmospheric pressure. The result obtained was a reaction product which, according to gas chromatography analysis and a distillation analysis, had the following composition (water not included):

Tri-n-butylamine: 28% by weight
Di-n-butylamine: 1% by weight
n-Butanol: 71% by weight Unknown byproducts and high boilers accounted for less than 0.4% by weight.

Reacting n-octanol with ammonia in a molar ratio of 7:1 under the same reaction conditions gave tri-n-octylamine in a yield of over 95 mol%. The 2.5% by weight of di-n-octylamine formed at the same time were separated quantitatively from the reaction product, added to fresh feed and alkylated with octanol. The resulting reaction mixture likewise contained the secondary amine in amount of about 2% by weight, so that in the steady state where the secondary amine formed is being returned again and again the reaction to the tertiary amine was virtually quantitative.

EXAMPLE 4

A stirred vessel having a capacity of 3,000 ml was charged with 592 of n-butanol, 17 g of ammonia, 5.5 g of calcium hydroxide and 55 g of metallic copper catalyst.

The copper catalyst has been prepared beforehand in a separate reaction at 200° C. from copper formate in the presence of dimethylamine-satured lauryl alcohol (cf. EP-B-70,512). Adhering secondary constituents had beforehand been removed from the catalyst by washing with n-butanol.

At 20° C. the stirred vessel was injected with 100 bar of hydrogen, and then heated to 220° C. The total pressure of the reaction system rose to 150–160 bar.

The system was stirred at 220° C. for 6 hours and then cooled down, the catalyst was allowed to settle, and the supernatant clear solution was drawn off. This solution had approximately the following composition (water not included):

Tri-n-butylamine: 28% by weight
Di-n-butylamine: 0.5% by weight
n-Butanol: 71% by weight
Unknowns: 0.5% by weight

We claim:

1. In a process for preparing a trialkylamine by reacting a primary alcohol with ammonia in the presence of a hydrogenation/dehydrogenation catalyst and in the presence of hydrogen, the improvement which comprises:
   (a) operating in liquid phase;
   (b) using the alcohol in a stoichiometric excess of from 1 to 15 moles per mole of ammonia;
   (c) carrying out the reaction at a temperature of from 190° to 280° C., at a total pressure of from 50 to 300 bar and in the presence of the water formed in the course of the reaction; and
   (d) using a hydrogenation/dehydrogenation catalyst which consists essentially of copper as the catalytically hydrogenating/dehydrogenating metal.

2. A process as claimed in claim 1, wherein the reactants are reacted in the presence of an alkali metal oxide and/or hydroxide and/or alkaline earth metal oxide and/or hydroxide.

3. A process as claimed in claim 2, wherein the alkali metal oxide and/or hydroxide and/or alkaline earth metal oxide and/or hydroxide is used in an amount of from 0.01 to 1, in particular from 0.02 to 0.2,% by weight, based on the amount of reactants.

4. A process as claimed in claim 1, wherein in $C_1$–$C_{24}$-alcohols are used in pure form or in the form of their mixtures.

5. A process as claimed in claim 1, wherein the stoichiometric excess of the alcohol over ammonia or the amine ranges from 1.5 to 15, preferably from 2 to 10, moles.

6. A process as claimed in claim 1, wherein the reaction temperature ranges from 200° to 240° C.

7. A process as claimed in claim 1, wherein the reaction is carried out under a total pressure of from 50 to 200, bar.

8. A process as claimed in claim 1, wherein the catalyst used is obtainable by thermal decomposition and reduction of a basic copper aluminum carbonate formed by precipitating a solution containing copper and aluminum salts at pH 8 to 10.

9. A process as claimed in claim 1, wherein the copper catalyst used is obtainable by heating copper formate at about 170° C. in the presence of an alcohol and dimethylamine.

10. A process as claimed in claim 1, wherein the alcohol:ammonia ratio changes from 4:1 to 18:1.

* * * * *

UNITED STATES PATENT AND TRADEMARK OFFICE
CERTIFICATE OF CORRECTION

PATENT NO.  : 4,851,578
DATED       : July 25, 1989
INVENTOR(S) : Roman Fischer and Herbert Mueller It is certified that error appears in the above-identified patent and that said Letters Patent is hereby corrected as shown below:

IN THE CLAIMS:

Claim 9, line 3:. change "about" to --above--.

Claim 10, line 2: change "changes" to --ranges--.

Signed and Sealed this

Eighth Day of May, 1990

Attest:

HARRY F. MANBECK, JR.

*Attesting Officer*     *Commissioner of Patents and Trademarks*